United States Patent
Jiang et al.

(10) Patent No.: US 7,183,091 B2
(45) Date of Patent: Feb. 27, 2007

(54) SULFITE REDUCTASE, THE PROCESS FOR PRODUCING THE SAME AND THE USE THEREOF

(75) Inventors: Shann-Tzong Jiang, Taipei (TW); Li-Jung Yin, Taipei (TW)

(73) Assignee: Nugen Bioscience (Taiwan) Co., Ltd., Taipei (TW)

( * ) Notice: Subject to any disclaimer, the term of this patent is extended or adjusted under 35 U.S.C. 154(b) by 423 days.

(21) Appl. No.: 10/453,093

(22) Filed: Jun. 3, 2003

(65) Prior Publication Data

US 2004/0161834 A1 Aug. 19, 2004

(30) Foreign Application Priority Data

Mar. 24, 2003 (TW) ............... 92106528 A

(51) Int. Cl.
*C12N 9/02* (2006.01)
(52) U.S. Cl. .................................... 435/189
(58) Field of Classification Search ............ None
See application file for complete search history.

(56) References Cited

U.S. PATENT DOCUMENTS 6,143,556 A * 11/2000 Trachtenberg ........... 435/289.1

OTHER PUBLICATIONS

Jiang et al. "Purified NADPH-sulfite reductase from *Saccharomyces cerevisiae* effects on quality of ozonated Mackerel Surimi" Journal of Food Science 1998, 63: 777-781. entire document.*
*Journal of Food Science*, A Publication of the Institute of Food Technologists, Nov./Dec. 2002, vol. 67, Nr. 9, 6 pages.
*Purification and Characterization of Escherichia Coli Sulfite Reductase and its Application in Surimi Processing*, Journal of Food Science, vol. 67, Nr. 9, 2002, pp. 3329-3334.

* cited by examiner

*Primary Examiner*—Sandra E. Saucier
*Assistant Examiner*—Satyendra K. Singh
(74) *Attorney, Agent, or Firm*—Scully, Scott, Murphy & Presser, P.C.

(57) ABSTRACT

The present invention relates to a purified sulfite reductase which has the following characteristics:
a. It functions to catalyze the reduction of sulfites to sulfides or to recover the sulfhydryl groups from disulfide groups,
b. In the aforesaid catalysis of the reduction, reduced nicotinamide dinucleotide phosphate (NADPH), methyl viologen (MVH) or other donors acts as an electron donor,
c. Its molecular weight is from 100,000 to 400,000,
d. The optimal temperature for its activity is from 20° C. to 30° C., and
e. The optimal pH for its activity is from 6.5 to 8.0.

The present invention also relates to a process for producing the purified sulfite reductase, and a method for recovering the proteins of denatured fish by using said sulfite reductase in solution or powder form.

8 Claims, 6 Drawing Sheets

SULFITE REDUCTASE, THE PROCESS FOR PRODUCING THE SAME AND THE USE THEREOF

BACKGROUND OF THE INVENTION

1. Technical Field (Field of the Invention)

The present invention relates to a purified sulfite reductase. More specifically, the sulfite reductase of the present invention catalyzes the reduction of sulfites to sulfides, effectively recovers the protein of the denatured fish meat when used in the denatured fish, and increases the number of reactive sulfhydryl groups and gel strength of the denatured fish protein. The present invention also relates to a process for producing the purified sulfite reductase, and the method for recovering the proteins of the denatured fish by using said sulfite reductase in solution or powder form.

2. Prior Art

Sulfite reductases extensively existing in plants and microorganisms are the enzymes catalyzing the reduction of sulfites to sulfides in the final step of assimilatory sulfate reductions, that is the key step of cysteine biosyntheses. During the reduction of sulfites to sulfides, where 6 electrons are provided in the reaction as follows: $SO_3^{2-}+6e^-+6H^+ \to S^{2-}+3H_2O$, reduced nicotinamide adenine dinucleotide phosphate (NADPH) acts as the electron donor in *Escherichia coli*, NADPH or reduced methyl viologen (MVH) acts as the electron donor in yeast, and other donors in other organisms or tissues.

Muscle proteins are mostly proteins of numerous types with various physiological functions, formed by the interactions of L-amino acids via peptide bonds, disulfide bonds, hydrogen bonds, ionic bonds and hydrophobic bonds, and by the actions via dipole-dipole moments. The "denaturation of proteins" refers to changes in the secondary, tertiary and quaternary three-dimensional structures of the proteins without destroying peptide bonds.

Because the structures of denatured proteins form random helix in unfolded states or aggregated states with the functional groups on or between peptide chains interacting thereby losing the original physical, chemical and biological characteristics. The reasons for the protein denaturation is generally considered as follows: the moisture in the muscle is frozen which makes salt concentration raised, and the environment pH value around the proteins changed, thereby resulting in the precipitation of protein molecules due to salting out and the aggregation of hydrophobic groups between or in molecules aggregate, and at the same time, new hydrogen bonds, disulfide bonds and ionic bonds are formed, which renders the proteins aggregated and in turn denatured. In addition, water surrounding the protein molecules form combined water with the functional groups such as —SH, —COOH, —NH and —CO of the protein molecules. In addition, due to temperature drop, water molecules with lower bonding strength form ice crystals first. At the same time, due to volume expansion, the conformation of protein molecules changes, the functional groups are exposed, new bonds are formed intermolecularly or intramolecularly, thereby causing protein molecules aggregated and denatured.

It is proven that the reason why the denaturation of freeze-stored fish proteins results in the formation of covalent bonds is that sulfhydryl groups are oxidized to disulfide groups (Jiang et al., J. Food Sci. 63:777–781, 1998, Jiang et al., J. Food Sci. 60:652–655, 1998). In denatured fish meat caused by freeze-storing, not only the phenomena such as softening of fish meat, running-off of tissue fluid, formation of spongy tissues formation occur, but also the emulsification property, water-holding capacity, gel-forming ability and viscoelasticity are all worse than those of fresh fish. The reason for these deteriorations is mainly because of the denaturation of myofibrillar proteins.

After being denatured, proteins form regular network structures, which make muscle proteins have characteristic of elasticity after being set by heat. Gelation of fish proteins, by which elasticity is given to the fish proteins, is one of the most important characteristics during processing fish proteins into refined products. The gelation of proteins is influenced by many factors, such as salt concentration, pH value, temperature, protein concentration, components, additives, ionic strength, freshness, and so on. It is known from the biochemical characteristics of the refined products that the bonds for forming network structures include hydrogen bonds, hydrophobic bonds, ionic bonds, disulfide bonds and other covalent bonds.

In addition, gel strength is an index to determine the quality of refined products of surimi. The elasticity of refined products is influenced by many factors, such as salt concentration, pH value, temperature, protein concentration, components, additives, ionic strength, freshness, and so on. Therefore, there have been proposed various methods to enhance the elasticity of the refined products of fish meat.

The gel-forming ability of fish meat decreases during freezing storage. The reason is mainly because of the gradual decrease in solubility of fish muscle proteins, which is considered resulting from the formation of polymers such as dimers and multimers of myosins due to the formation of disulfide and other covalent bondings. The formation of disulfide bonds among muscle proteins results in the aggregation and denaturation of actomyosin of fish muscle.

As described above, the gel-forming ability of fish meat decreases during freezing storage that causes the fish meat unsuitable for the processing of protein colloidal foods. The applications of freeze-stored fish meat in the production of protein colloidal foods are thus limited.

Although an alkaline washing treatment has long been employed to improve the gel-forming ability of mackerel surimi, it does not benefit color improvement. Although increase in alkaline washing cycles or using ozonic bleaching could substantially improve the color of mackerel, it results in deteriorations of gel-forming properties of the mackerel muscle proteins.

In addition, as for frozen surimi obtained by adding chemical reducing agents such as cysteine, sodium disulfite, ascorbic acid, and so on, into denatured fish muscles, the total sulfhydryl groups and reactive sulfhydryl groups of actomyosins, and the amount of extractable actomyosins are all much higher than those of frozen surimi to which the reducing agents are not added. Although the gel-forming ability of proteins decreases due to freezing, the addition of reducing agents could recover most of the proteins. Therefore, it is shown that reducing agents could recover the aggregated and denatured actomyosins. The addition of reducing agents results in reducing disulfide bonds of frozen denatured fish meat to sulfhydryl bonds during grinding. The disulfide bonds are re-formed during gelation of refined products whereby the network structures become more firm and stable. However, the chemical reducing agents are considered as external additives and are not easy to accept by the consumers.

The inventors of the present invention proposed to use sulfite reductases derived from microorganisms to replace those chemical reducing agents. For instance, Jiang et al. investigated the effect of sulfite reductases from yeasts on recovering denatured fish muscle protein of ozonically decolored/denatured and frozen denatured mackerel surimi, and found that the crude sulfite reductase could recover the denatured muscle proteins and enhance the gel-forming ability of refined products (Jiang et al., J. Food Sci. 60: 652–655, 1998; Jiang et al., J. Food Sci. 60: 777–781, 1998). Furthermore, Wu et al. applied crude lyophilized powders of the sulfite reductase prepared from *Saccharomyces cerevisiae*, applied to the processing of frozen fish, and also found that the gel-forming ability of refined products were substantially enhanced (Wu et al., J. Food Sci. 65: 1400–1403, 2000). However, sulfite reductases from microorganisms have never been prepared, the effects thereof on the recovery of denatured fish muscles have never been investigated, either.

SUMMARY OF THE INVENTION

In order to overcome the aforementioned problems in the prior art, the inventors of the invention investigated methods for producing sulfite reductases derived from microorganisms and the effects of the obtained sulfite reductases on recovering native muscle proteins of the denatured fish meat, and found that the aforementioned purpose could be achieved by the use of the purified sulfite reductase from *Escherichia coli* or a species of Saccharomyces. The present invention was completed thereby.

The present invention therefore provides a purified sulfite reductase characterized by having the following characteristics:

a. It functions to catalyze the reduction of sulfites to sulfides or to recover the sulfhydryl groups from disulfide groups,
b. In the aforesaid catalysis of the reduction, reduced nicotinamide dinucleotide phosphate (NADPH), methyl viologen (MVH) or other donors acts as an electron donor,
c. Its molecular weight is from 100,000 to 400,000,
d. The optimal temperature for its activity is from 20° C. to 30° C., and
e. The optimal pH for its activity is from 6.5 to 8.0.

Preferably, of the electron donor the sulfite reductase is NADPH. In addition, the sulfite reductase is preferably derived from *Escherichia coli* or a species of *Saccharomyces*. The species of *Saccharomyces* may be *Saccharomyces cerevisiae*, *Saccharomyces bayanus*, *Saccharomyces ellipsoideus*, and *Saccharomyces aceti*. Of the foregoings, *Saccharomyces cerevisiae* is the preferable one.

In addition, the present invention also provides process for producing a purified sulfite reductase characterized by employing ammonium sulfate fractionation and chromatography to purify a sulfite reductase from a crude enzyme solution of *Escherichia coli* or a species of *Saccharomyces*.

In the process for producing the purified sulfite reductase, the crude enzyme solution is produced by the following steps: adding a phosphate buffer of pH 6.5 to 8.5 to the cells of *Escherichia coli* or a species of *Saccharomyces*; disrupting the cells for 0.1 to 2 hours at a temperature of 2 to 10° C. using an ultrasonic sonicator; collecting the supernatant liquid after centrifugation for 30 minutes at 5,000×g; suspending the residual debris cells in the same buffer followed by grinding the debris cells; collecting the supernatant liquid after centrifugation as mentioned above; combining the supernatant liquids.

Further, the ammonium sulfate fractionation comprises the following steps: gently adding ammonium sulfate to the crude enzyme solution which is produced as described in claim 6; collecting the precipitate at 30 to 60% saturation after centrifugation at a rate of 3,000 to 15,000×g for 0.1 to 2 hours, dialyzing the solution of the precipitate against a 0.1 to 0.2 M phosphate buffer (pH 6.5–8.5) to obtain a dialysate, all the steps being performed at 2° C. to 10° C.

Moreover, the chromatography is selected from the group consisting of DEAE Sephacel column chromatography and/or Sephacryl S-300 HR column chromatography.

The present invention also provides a method for recovering the proteins of denatured fish, comprising applying to the proteins of the denatured fish. The sulfite reductase of the present invention can be used in solution or powder form in an amount of 0.01 to 0.5 active units of sulfite reductase per gram of the proteins of the denatured fish. The time for the sulfite reductase in solution or powder form to act on the proteins of the denatured fish is 5 to 40 minutes.

DETAILED DESCRIPTION OF THE INVENTION AND PREFERRED EMBODIMENTS

Figure 1:
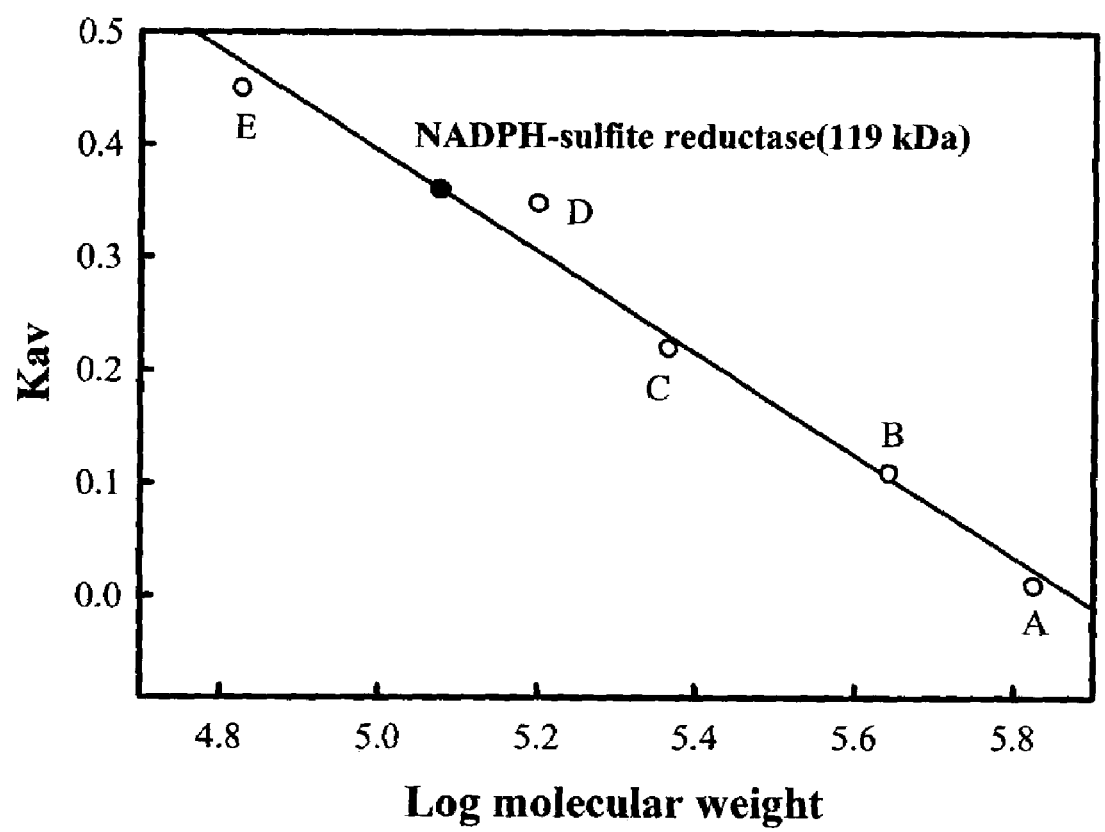
FIG. 1 shows the calibration curve for determining the molecular weight of the sulfite reductase from *Escherichia coli* by using Sephacryl S-300 HR gel permeation column chromatography. In the figure, point A represents thyroglobulin (669 kDa), point B represents ferritin (440 kDa), point C represents catalase (232 kDa), point D represents aldolase (158 kDa), and point E represents bovine serum albumin (67 kDa)

In the present invention, the sulfite reductases, the raw enzyme solution thereof and the raw enzyme powders thereof were obtained from *Escherichia coli* or *Saccharomyces cerevisiae*. Further, the effects of the above enzymes on recovering the protein of denatured fish meat were also investigated.

The materials and equipments employed, the production of sulfite reductases and related experimental or testing methods are described first.

(A) Materials and Equipments (1) Bacteria and Yeast Cells

1. In an Erlenmeyer flask a culturing medium containing 4.0% sucrose, 0.4% yeast extract and 0.4% tryptone (pH 7.5) was inoculated with a loop of 1% of activated *Escherichia coli* (CCRC 11634) purchased from Taiwan Culture Collection and Research Center (Hisnchu, Taiwan), and cultured at 37° C. for 18 hours with shaking at 100 rpm. *Escherichia coli* cells were collected by centrifugation at 5,000×g for 30 minutes.

2. In an Erlenmeyer flask a YM broth culturing medium containing 0.3% yeast extract, 0.3% malt extract, 0.5% peptone and 1.0% dextrose (pH 7.0) was inoculated with a loop of *Saccharomyces cerevisiae* (CCRC 22223) persuaded from Taiwan Culture Collection and Research Center (Hisnchu, Taiwan), and cultured at 24° C. for 60 hours with shaking at 100 rpm. *Saccharomyces cerevisiae* cells were collected by centrifugation at 4,000×g for 30 minutes.

(2) Reagents

DEAE Sephacel, Sephacryl S-300 HR, electrophoresis molecular weight standards and gel permeation filtration molecular weight standards were purchased from Pharmacia Biotech (Uppsala, Sweden).

Yeast extract, tryptone were purchased from Difco.

Ammonium sulfate was purchased from Merck (Darmstadt, Germany).

Bovine serum albumin (BSA), flavin mononucleotide (FMN), reduced nicotinamide adenine dinucleotide phosphate (NADPH), glutathione, dithiothreitol, cysteine, 5,5'-dithiobis-(2-nitrobenzoic acid) (DTNB), β-mercaptoethanol (β-Me), and sodium dodecyl sulfate (SDS) were purchased from Sigma Chemical Co. (St. Louis, Mo., U.S.A.).

Iodoacetate (IAA), N-ethylmaleimide (NEM), p-chloromercuriphenylsulfonic acid (PCMPS), p-chloromercuribenzoate (PCMB), phenylmethylsulfonyl fluoride (PMSF), and N,N,N',N'-tetramethyl-ethylenediamine (TEMED) were purchased from Bio-Rad (Richmond, Calif., U.S.A.).

All other chemicals were biochemical reagent grade. (2) Instruments

1. Low temperature oscillation culturing box: Hotech 718 of Hotech Instruments Co., Taipei, Taiwan.

2. Low temperature and high speed centrifuge: SCR20B of Hitachi Co., Japan.

3. Ultrasonic sonicator: Model W-200 of Utrasonics Inc., Japan.

4. Physical property determinator: Model CR-200 of Sun Kagaku, Tokyo, Japan.

5. Spectrophotometer: Hitachi U-2001 of Hitachi Co., Japan.

6. Mini-electrophoresis: Mini-PROTEAN 11 cell, the power source supplier was Bio-Rad model 200/2.0 of Bio-Rad, U.S.A.

7. pH meter: HM-30S of TOA Electronic Co., Japan.

8. Water bath tank: Model B204 of MARATON, Taiwan.

9. Grinder: CF 5 kg of Chyau Far Co., Taiwan.

10. Columns: C26/40 and C26/100 of Pharmacia LKB Biotechnology, Uppsala, Sweden.

11. Fraction collector: FRAC-200 of Pharmacia LKB Bio-technology, Uppsala, Sweden.

12. Fast protein liquid chromatography (FPLC) system: Controller LCC-500 Plus and Pump P-500 of Pharmacia LKB Biotechnology, Uppsala, Sweden.

13. -20° C. Freezer: Bio-Freezer, Model 8442 of Forma Scientific, USA.

14. Amicon ultrafiltration condensation equipment: purchased from Amicon, USA, condensation tank (stirred cell Model 8050) and filtration film (YM 10 43 mm membrane) as its main structure.

15. Antifoam homogenizer: Waring blender subjoined with a baffle.

(B) Production and Purification of the Sulfite Reductase

Extraction. After being cultured in a medium containing 4.0% sucrose, 0.4% yeast extract and 0.4% tryptone (pH 7.5) at 37° C. for 18 h, *E. coli* cells were collected by centrifugation at 5,000×g for 30 min and mixed with 2-fold volume (relative to the volume of the cells) of 0.1 M potassium phosphate buffer containing 0.5 mM EDTA (pH 7.7). The collected cells were then disrupted at 4° C. for 30 min using a sonicator and collected by 30 min of centrifugation at 5,000×g. The resulting samples were suspended in a 0.1 M phosphate buffer (pH 7.7) and disrupted and centrifuged again as mentioned above. On the other side, after being cultured in a medium containing 0.3% yeast extract, 0.3% malt extract, 0.5% peptone and 1.0% dextrose (pH 7.0) for 60 hr, *Saccharomyces cerevisiae* cell was collected by 30 min centrifugation at 4,000×g. The cell was mixed with 2-fold volume (relative to the volume of the cells) 0.3 M potassium phosphate buffer containing 1 mM EDTA (pH 7.3) and disrupted with a Utrasonics model W-200 sonicator for 30 min at 4° C. Cells and debris were collected by 30 min centrifugation at 1,3000×g. The residue was suspended in a 0.3 M phosphate buffer (pH 7.0), disrupted and centrifuged again.

Ammonium sulfate fractionation. Solid ammonium sulfate was gently added to the crude enzyme with stirring. The precipitates at 30–60% saturation were collected by 30 min of centrifugation at 5,000×g and then dialyzed against 0.1 M phosphate buffer (pH 7.7) for 24 h. All procedures were performed at 4° C.

DEAE Sephacel column chromatography. The dialyzed crude enzyme was chromatographed on DEAE Sephacel (2.6×20 cm) which was equilibrated previously with 0.1 M phosphate buffer containing 0.5 mM EDTA (pH 7.7). After being washed with 10 volumes of phosphate buffer, the absorbed protein was eluted by a linear gradient of 0–1.0 M NaCl in 0.1 M phosphate buffer at a flow rate of 1 mL/min. Fractions of 5 mL were collected using a fraction collector. The crude reductase was eluted at NaCl concentration of 0.32–0.40 M.

Sephacryl S-300 HR column chromatography. Fractions with reductase activity on DEAE Sephacel chromatography was concentrated and equilibrated with 0.1 M phosphate buffer containing 0.5 mM EDTA (pH 7.7) using Amicon ultrafiltration. The resulting sample was applied onto the Sephacryl S-300 HR column (2.6×90 cm), which was previously equilibrated with 0.1 M phosphate buffer containing 0.5 mM EDTA (pH 7.7). The flow rate was 1 mL/min, and 5 or 2.5 mL per fraction was collected. This Sephacryl S-300 HR chromatography was performed 3 times. The purified enzyme was then stored at −70° C. until use.

(C) Tests For the Biochemical Characteristics of the Sulfite Reductase

Determination of Enzyme Activity

The sulfite reductase activity was measured spectrophotometrically at 340 nm under aerobic conditions by following the oxidation of NADPH by sulfite according to the method of determining enzyme activity of Siegel and others (1973). To 0.9 mL reaction mixture [0.1 M phosphate buffer (pH 7.7) containing 0.5 mM EDTA, 0.5 mM $NaHSO_3$, 1 μM FMN, and 0.2 mM NADPH], 0.1 mL of reductase was added and incubated at 25° C. The activity was determined according to the initial velocity after the addition of reductase and corrected by the slow oxidation of NADPH in the absence of sulfite. One activity unit was defined as the amount of enzyme which catalyzed the oxidation of 1 μmol NADPH within 1 minute reaction 25° C. under the above condition.

Determination of Protein Concentration

Protein concentration was determined by dye binding method. Bovine serum albumin was used as a marker.

Molecular Weight

The molecular weight of the sulfite reductase was determined using Sephacryl S-300 HR column chromatography. Thyroglobulin (669 kDa), ferritin (440 kDa), catalase (232 kDa), aldolase (158 kDa), and bovine serum albumin (67 kDa) were used as standard proteins.

Influence of Temperature and pH

Optimal temperature. To 0.9 mL reaction mixture [0.1 M phosphate buffer (pH 7.7) containing 0.5 mM EDTA, 0.5 mM NaHSO$_3$, 1 μM FMN, and 0.2 mM NADPH], 0.1 mL of reductase was added and incubated at various temperatures (5, 10, 15, 20, 25, 30, 35, 40, 45, 50, 55 and 60° C.) for 5 minutes. The activity was determined from initial velocity and corrected by the oxidation of NADPH in the absence of sulfite according the method of Siegel and others (1973).

Thermal stability. Purified sulfite reductase in 0.1 M phosphate buffer (pH 7.7) was incubated at various temperatures (5, 10, 15, 20, 25, 30, 35, 40, 45, 50, 55 and 60° C.) for 30 minutes. The residual activity was measured according the method of Siegel and others (1973).

Optimal pH value. To 0.9 mL reaction mixture with various pHs (0.2 M citrated buffer: pH 4.0 to 6.0; 0.2 M phosphate buffer: pH 6.0 to 8.0 and 0.2 M bicarbonate buffer: pH 8.0 to 10,0; all buffers containing 0.5 mM EDTA, 0.5 mM NaHSO$_3$, 1 μM FMN, and 0.2 mM NADPH), 0.1 mL of reductase was added and incubated at 25° C. for 5 minutes. The activity was determined from initial velocity and corrected by the oxidation of NADPH in the absence of sulfite according to the method of Siegel and others (1973).

pH stability. Purified sulfite reductase in buffers with various pHs (0.2 M citrated buffer: pH 4.0 to 6.0; 0.2 M phosphate buffer: pH 6.0 to 8.0 and 0.2 M bicarbonate buffer: pH 8.0 to 10,0) was incubated at 25° C. for 30 minutes. The residual activity was determined according the method of Siegel and others (1973).

Effects of Metal Ions or Inhibitors

Purified sulfite reductase in 0.1 M phosphate buffer (pH 7.7) and various metals or inhibitors was incubated at 25° C. Final concentrations of the metals were 0.5, 1.0, 5.0 and 10.0 mM and that of inhibitors was 1.0 mM. After 30 minutes of incubation, the remaining activity was measured according the method of Siegel and others (1973).

Stability of Low Temperature Storage

The enzyme solution was stored at 4° C. and −20° C., respectively. The residue enzyme activity was determined per constant time interval to test the stability of low-temperature storage.

(D) Recovery Tests of Frozen Denatured Fish Muscle of Mackerel, Golden Thread and Largehead Hairtail Preparation of Frozen Surimi of Mackerel, Golden Thread and Largehead Hairtail Fish muscle of mackerel, Golden thread and Largehead hairtail as raw material was stored in a freezer at −25° C. for 6 months storage to be frozen denatured. The frozen fish muscle was gutted, deboned, and then rinsed with ice water 3 times, centrifuged by a centrifugal dewaterer to a moisture content of about 78%. The obtained surimi was grinded for 10 minutes, and mixed with 0.2% polyphosphates and 5% saccharides or glycitols, put in a blast freezing apparatus at −40° C. to make the central temperature lower to −18° C., frozen rapidly, and then stored in a freezing storage for later use.

Production of Refined Product

The aforementioned frozen surimi was put in an air-conditioned room to make the central temperature raise to −2 to −5° C., unfrozen, and then the sulfite reductase, the raw enzyme solution thereof or the raw enzyme powders thereof obtained above was added. At the same time, the surimi was grinded by grinder after adding 2.5% salt, and then was grinded for 20 minutes again. At last, 3% potato starch was added and mixed homogeneously. The resultant was stuffed into a casing, placed still at 25° C. for 30 minutes, and then heated at 95° C. for 20 minutes. After the resultant was cooled with flowing water, it was stored at 4° C., and the properties thereof were determined the next day.

Determination of the Properties of Surimi

Actomyosin from surimi was extracted according to the method of Noguchi and Matsumoto (1978). The reactive groups of atomyosin were determined according to the improved method of Itoh and others (1979). The gel-forming ability was determined by cutting the refined product of surimi into 3.0 cm height and determining the gel strength by using a physical property determinator, which has a plug of a 5 mm diameter.

Preparation of Actomyosin From Surimi and Determination of SH

Actomyosin (AM) was extracted according to the method of Noguchi and Matsumoto (1978). Actomyosin in 50 mM phosphate buffer (pH 7.0) containing 0.6 M KCl and 6 mM EDTA were mixed with 0.01 M DTNB solution and incubated at 5° C. for 1 hour. The reactive SH was determined according to Itoh and others (1979).

Determination of Gel Strength

The gel strength was determined by a Rheometer and expressed as the breaking force (g) and deformation (cm) [gel strength (g×cm)=breaking force (g)×deformation (cm)].

Statistical Analysis

Duncan's multiple range test was employed for statistical analysis. For gel strength, 10 determinations from each group were analyzed. Significance of differences was defined at $p<0.05$.

(E) EXAMPLES

The following preparation examples and use examples are illustrated to describe the present invention more specifically. However, the present invention is not intended to be limited by these examples.

Preparation Example 1

Extraction and Purification and Biochemical Characteristics of the Sulfite Reductase from *Escherichia coli*

To one part by volume of *Escherichia coli* cells (CCRC 11634), there were added two parts by volume of 0.1 M potassium phosphate containing 0.5 mM EDTA (pH 7.7). The cells were disrupted at 4° C. for 30 minutes using an ultrasonic sonicator of 30% output power and dyed. A microscope was used to observe whether the cells were disrupted completely or not. The cells-buffer mixture was then centrifuged for 30 minutes at 5,000×g. The supernatant liquid was collected. A same part by volume of the same phosphate buffer solution was added into the residual disrupted cells. The resultant was ground and centrifuged again in the same way to collect the supernatant crude enzyme solution.

The collected supernatant crude enzyme solutions were combined. Solid ammonium sulfate was gently added to the crude enzyme solution with stirring. It was found that the precipitates at 30 to 60% saturation had the highest activity. Thus precipitates at 30 to 60% saturation were collected and dissolved in 0.1 M phosphate buffer and was then dialyzed against 0.1 M phosphate buffer solution (pH 7.7) for 24 hours. All procedures were performed at 4° C.

The dialyzed crude enzyme was chromatographed on DEAE Sephacel (2.6×20 cm) which was equilibrated previously with 0.1 M phosphate buffer containing 0.5 mM EDTA (pH 7.7). After being washed with 10 volumes of phosphate buffer, the absorbed protein was eluted by a linear gradient of 0.1 M NaCl in 0.1 M phosphate buffer at a flow rate of 1 mL/min. Fractions of 5 mL were collected using a fraction collector. The crude reductase was eluted at NaCl concentration of 0.32–0.40 M.

Fractions with reductase activity on DEAE Sephacel chromatography was concentrated and equilibrated with 0.1 M phosphate buffer containing 0.5 mM EDTA (pH 7.7) using Amicon ultrafiltration. The resulting sample was applied onto the Sephacryl S-300 HR column (2.6×90 cm), which was previously equilibrated with 0.1 M phosphate buffer containing 0.5 mM EDTA (pH 7.7). The flow rate was 1 mL/min, and 5 or 2.5 mL per fraction was collected. This Sephacryl S-300 HR chromatography was performed 3 times. The purified enzyme was then stored at −70° C. until use.

After analysis, it was determined that the yield and the specific activity of sulfite reductase from *Escherichia coli* were 31.7% and 10.03 units/mg, respectively. In addition, a 579.5-fold-purification was achieved (as indicated in Table 1).

TABLE 1

Summary of the production and purification of sulfite reductase from *Escherichia coli*

| Step | Total protein (mg) | Total activity (units) | Specific activity (units/mg) | Yield (%) | Purification (fold) |
|---|---|---|---|---|---|
| Crude extract | 3660.1 | 63.27 | 0.017 | 100.0 | 1.0 |
| 30 to 60% (NH$_4$)$_2$SO$_4$ | 1401.6 | 44.23 | 0.032 | 69.9 | 1.8 |
| DEAE-Sephacel | 599.5 | 35.25 | 0.059 | 55.7 | 3.4 |
| 1st Sephacryl S-300 HR | 34.2 | 30.00 | 0.877 | 47.4 | 50.7 |
| 2nd Sephacryl S-300 HR | 15.8 | 25.98 | 1.644 | 41.1 | 95.1 |
| 3rd Sephacryl S-300 HR | 2.0 | 20.05 | 10.025 | 31.7 | 579.5 |

The biochemical characteristics of the sulfite reductase from *Escherichia coli* were as follows.

(1) Molecular Weight

The molecular weight of the sulfite reductase from *Escherichia coli* was 119,000, estimated by Sephacryl S-300 HR gel filtration column chromatography, in accordance with the calibration curves obtained from the standard proteins (as indicated on FIG. 1).

(2) Optimal pH Value and pH Stability

Figure 2:
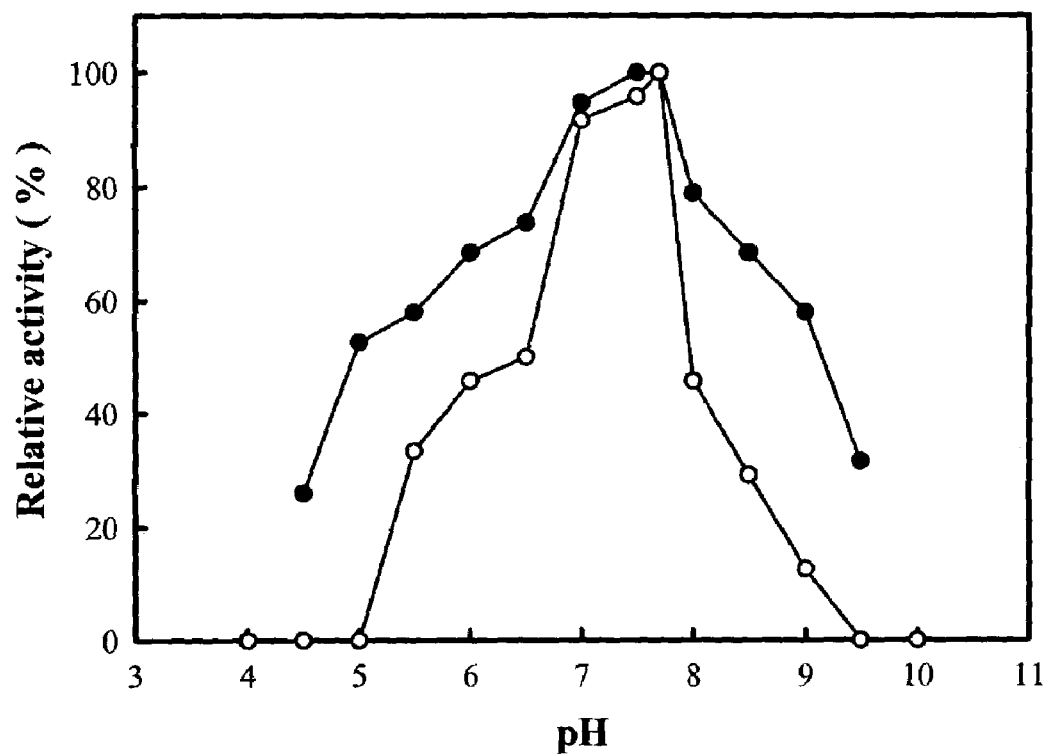
FIG. 2 shows the effects of pH value on the activity of the sulfite reductase from *Escherichia coli*. In the figure, "○" represents the pH-dependent activity, and "●" represents the stability at the indicated pH.

The sulfite reductase from *Escherichia coli* had an optimum pH at 7.7 and was very stable at pH 6.5 to 8.0 (as indicated on FIG. 2). The activity of the sulfite reductase was determined after being allowed to stand at 25° C. and pH 4.0 to 10.0. It was found that, at pH 6.5 to 7.5, there was still more than 95% activity left, at pH 6.5, there was still more than 73.7% activity left, and at pH 8.0, there was still more than 79.0% activity left. Therefore, it was known that the stability of the enzyme was better in neutral conditions than in slightly acidic or alkaline condition.

(3) Optimal Temperature and Thermal Stability

Figure 3:
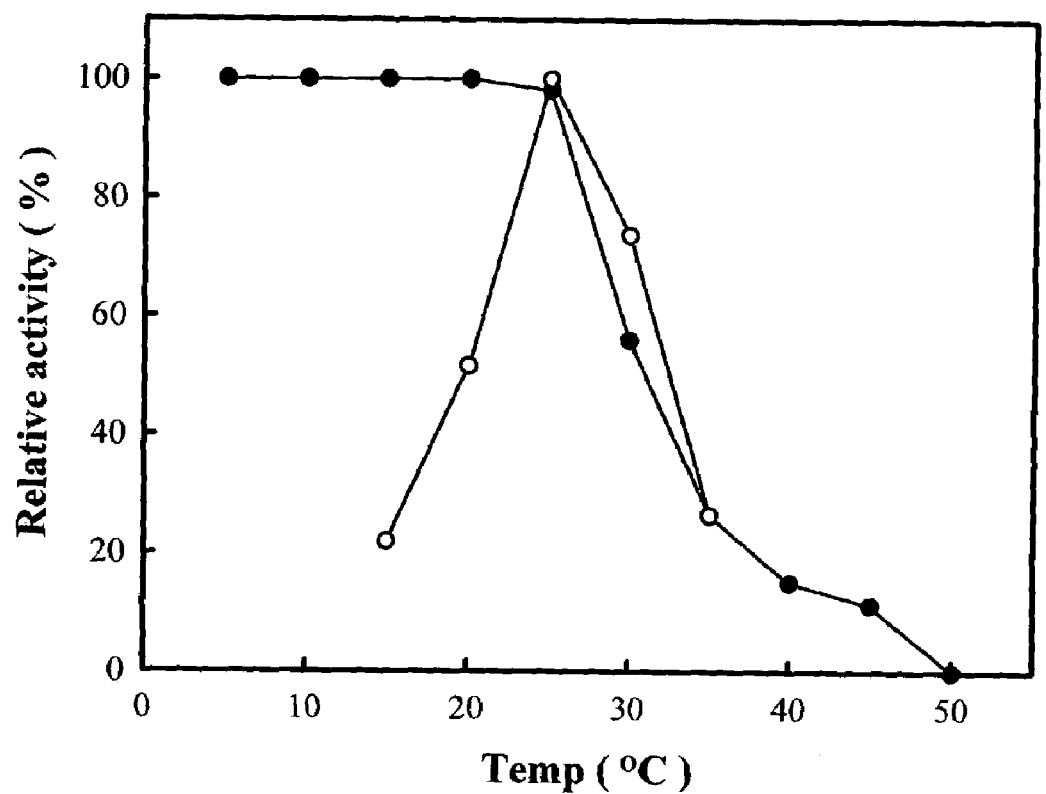
FIG. 3 shows the effects of temperature on the stability of the sulfite reductase from *Escherichia coli*. In the figure, "○" represents the temperature-dependent activity, and "●" represents the stability at the indicated temperatures.

The sulfite reductase from *Escherichia coli* had an optimum temperature at 25° C. As for thermal stability, the enzyme was very stable at the temperature ranging from 5 to 25° C., and there was still more than 98.0% activity left. When the temperature was above 25° C., the enzyme was inactivated gradually, and was inactivated completely while achieving 50° C. (as indicated on FIG. 3).

(4) Effects of Inhibitors on Enzyme Activity

The catalytic activity of the sulfite reductase from *Escherichia coli* was completely inhibited by PCMB and KCN, partially by NEM, PMSF, and IAA.

(5) Effects of Metal Ions on Enzyme Activity

The catalytic activity of the sulfite reductase from *Escherichia coli* was strongly inhibited by $Hg^{2+}$, $Fe^{2+}$, $Fe^{3+}$, $Ca^{2+}$, $Co^{2+}$, and $Cu^{2+}$, and moderately by $Cd^{2+}$, $Zn^{2+}$, $Mn^{2+}$, $Ba^{2+}$. However, $Na^+$, $K^+$, and $Mg^{2+}$ did not affect the enzyme activity. Among the metal ions, $Hg^{2+}$, $Fe^{2+}$, $Cu^{2+}$, and $Zn^{2+}$ would interact with sulfhydryl groups on the enzyme and inhibit the activity. According to the results of this item, it was proven that cysteine residue groups are contained on the active sites of the enzyme.

(6) Effects of Reducing Agents on Enzyme Activity

The reducing agents such as glutathione, dithiothreitol, β-mercaptoethanol and cysteine all improved the activity of the sulfite reductase from *Escherichia coli*.

(7) Stability of Low-temperature Storage

The enzyme solution of the sulfite reductase from *Escherichia coli* was stored at temperatures of 4° C. and −20° C., respectively. The residual enzyme activity was determined per constant time interval. The results of testing showed that the enzyme activity was still 77.8% after being stored for 28 days at 4° C., and the activity had nearly not changed after being stored for 2 months at −20° C.

Preparation Example 2

Production, Purification and Biochemical Characteristics of the Sulfite Reductase from *Saccharomyces cerevisiae*

To one part by volume of *Saccharomyces cerevisiae* (CCRC 22223) cells there were added two parts by volume of a 0.3 M phosphate buffer solution containing 0.1 mM EDTA (pH 7.3). The cells were disrupted at 4° C. for 30 minutes using an ultrasonic sonicator of 30% output power and dyed. A microscope was used to observe whether the cells were disrupted completely or not. The cells-buffer mixture was then centrifuged for 60 minutes at 13,000×g. The supernatant liquid was collected. A same part by volume the same buffer solution was added into the residual disrupted cells. The disrupted cells were ground and centrifuged again in the same way to collect the supernatant.

The collected supernatant crude enzyme solutions were combined. Solid ammonium sulfate was gently added to the crude enzyme solution with stirring. It was found that the precipitates of ammonium sulfate at 30 to 60% saturation had the highest activity. Thus precipitates at 30 to 60% saturation were dissolved in 0.1 M phosphate buffer solution (pH 7.7) and then dialyzed against the same buffer solution for 24 hours. All procedures were performed at 4° C.

The dialyzed crude enzyme was chromatographed on DEAE Sephacel (2.6×20 cm) which was equilibrated previously with 0.1 M phosphate buffer containing 0.5 mM EDTA (pH 7.7). After being washed with 10 volumes of phosphate buffer, the absorbed protein was eluted by a linear gradient of 0.1 M NaCl in 0.1 M phosphate buffer at a flow rate of 1 mL/min. Fractions of 5 mL were collected using a fraction collector. The crude reductase was eluted at NaCl concentration of 0.32–0.40 M.

Fractions with reductase activity on DEAE Sephacel chromatography was concentrated and equilibrated with 0.1 M phosphate buffer containing 0.5 mM EDTA (pH 7.7) using Amicon ultrafiltration. The resulting sample was applied onto the Sephacryl S-300 HR column (2.6×90 cm), which was previously equilibrated with 0.1 M phosphate buffer containing 0.5 mM EDTA (pH 7.7). The flow rate was 1 mL/min, and 5 or 2.5 mL per fraction was collected. This Sephacryl S-300 HR chromatography was performed 3 times. The purified enzyme was then stored at −70° C. until use.

After analysis, it was determined that the yield and the specific activity of sulfite reductase from *Saccharomyces cerevisiae* were 14.2% and 1.34 units/mg, respectively. In addition, a 432.3-fold-purification was achieved (as indicated in Table 2).

TABLE 2

Summary of the production, purification of sulfite reductase from *Saccharomyces cerevisiae*

| Step | Total protein (mg) | Total activity (units) | Specific activity (units/mg) | Yield (%) | Purification (fold) |
|---|---|---|---|---|---|
| Crude extract | 4184.3 | 30.76 | 0.0031 | 100 | 1.0 |
| 30–50% (NH$_4$)$_2$SO$_4$ | 1326.6 | 23.89 | 0.0181 | 77.7 | 5.8 |
| DEAE-Sephacel | 384.7 | 19.07 | 0.0236 | 62.0 | 7.6 |
| 1st Sephacryl S-300 | 250.9 | 14.46 | 0.0576 | 46.5 | 18.6 |
| 1st Sephadex A-50 | 31.84 | 9.54 | 0.2996 | 31.0 | 96.6 |
| 2nd Sephacryl S-300 | 21.28 | 7.38 | 0.3469 | 23.9 | 111.9 |
| 2nd Sephadex A-50 | 5.24 | 5.84 | 1.1145 | 19.0 | 359.5 |
| 3rd Sephadex A-50 | 3.22 | 4.31 | 1.34 | 14.2 | 432.3 |

The biochemical characteristics of the sulfite reductase from *Saccharomyces cerevisiae* were as follows.

(1) Molecular Weight

The molecular weight of the sulfite reductase from *Saccharomyces cerevisiae* was 358,000, estimated by Sephacryl S-300 HR gel filtration column chromatography, in accordance with the calibration curves obtained from the standard proteins.

(2) Optimal pH Value and pH Stability

The sulfite reductase from *Saccharomyces cerevisiae* had an optimum pH value at 7.3 and was very stable at pH 6.5 to 7.5.

(3) Optimal Temperature and Thermal Stability

The sulfite reductase from *Saccharomyces cerevisiae* had an optimum temperature at 25° C., and was very stable in the temperature range of 5 to 30° C.

(4) Effects of Inhibitors on Enzyme Activity

The catalytic activity of the sulfite reductase from *Saccharomyces cerevisiae* was completely inhibited by PCMPS, PCMB and KCN, and partially by NEM, PMSF, and IAA.

(5) Effects of Metal Ions on Enzyme Activity

The catalytic activity of the sulfite reductase from *Saccharomyces cerevisiae* was strongly inhibited by $Hg^{2+}$, $Zn^{2+}$, $Pb^{2+}$, and $Cu^{2+}$, and partially by $Co^{2+}$, $Ni^{2+}$, $Fe^{2+}$, $Mn^{2+}$ and $Ba^{2+}$. However, $Na^+$, $K^+$, $Ca^{2+}$, and $Mg^{2+}$ did not affect the enzyme activity.

(6) Effects of Reducing Agents on Enzyme Activity

The reducing agents such as glutathione, dithiothreitol, β-mercaptoethanol and cysteine all improved the activity of the sulfite reductase from *Saccharomyces cerevisiae*.

(7) Stability of Low-temperature Storage

The enzyme solution of the sulfite reductase from *Saccharomyces cerevisiae* was stored at temperatures of 4° C. and −20° C., respectively. The residue enzyme activity was determined per constant time interval. The results of testing showed that the enzyme activity was still 77.8% after being stored for 28 days at 4° C., and the activity had nearly not changed after being stored for 2 months at −20° C.

Use Example 1

Figure 4:
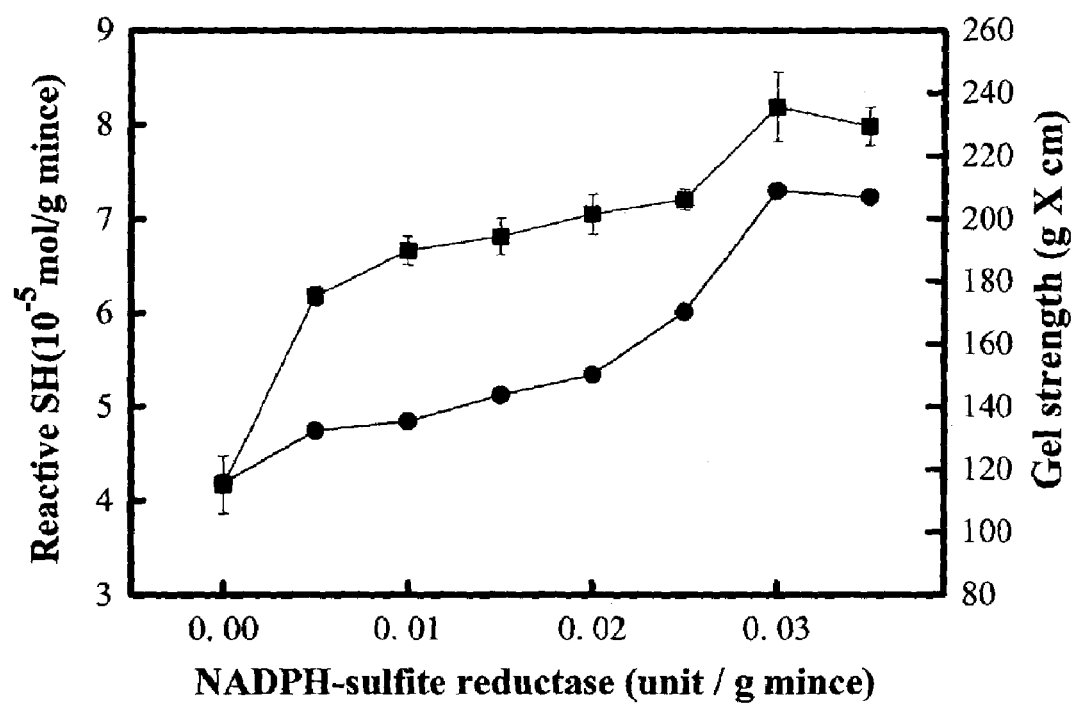
FIG. 4 shows the effects of the amount of the sulfite reductase from *Escherichia coli* added on the number of the reactive sulfhydryl groups and the strength of the gel of frozen denatured mackerel surimi. In the figure, "●" represents the number of the reactive sulfhydryl groups, and "■" indicates the gel strength.

Effects of the Sulfite Reductase from *Escherichia coli* on Frozen Denatured Mackerel Surimi The effects of the amount of the sulfite reductase from *Escherichia coli* added on the number of the reactive sulfhydryl groups and gel strength in frozen denatured mackerel surimi were indicated in FIG. 4. Various active units of the sulfite reductase from *Escherichia coli* were added into frozen denatured mackerel surimi. The reactive sulfhydryl groups increased obviously with the increase of the amount of the reductase added. When 0.03 active units/g mince of the sulfite reductase was added, the number of the reactive sulfhydryl groups in mackerel surimi increased from $4.19 \times 10^{-5}$ to $7.23 \times 10^{-5}$ mol/g mince. No obvious change in the reactive sulfhydryl groups was observed when the added reductase was higher than 0.03 units/g mince. Similar trends were also observed in the changes of the gel strength. The gel strength increased from 115.0 g×cm to 235.7 g×cm, when 0.03 units/g mince of the sulfite reductase from *Escherichia coli* was added. No obvious change in the gel strength was observed when the reductase added was higher than 0.03 units.

Figure 5:
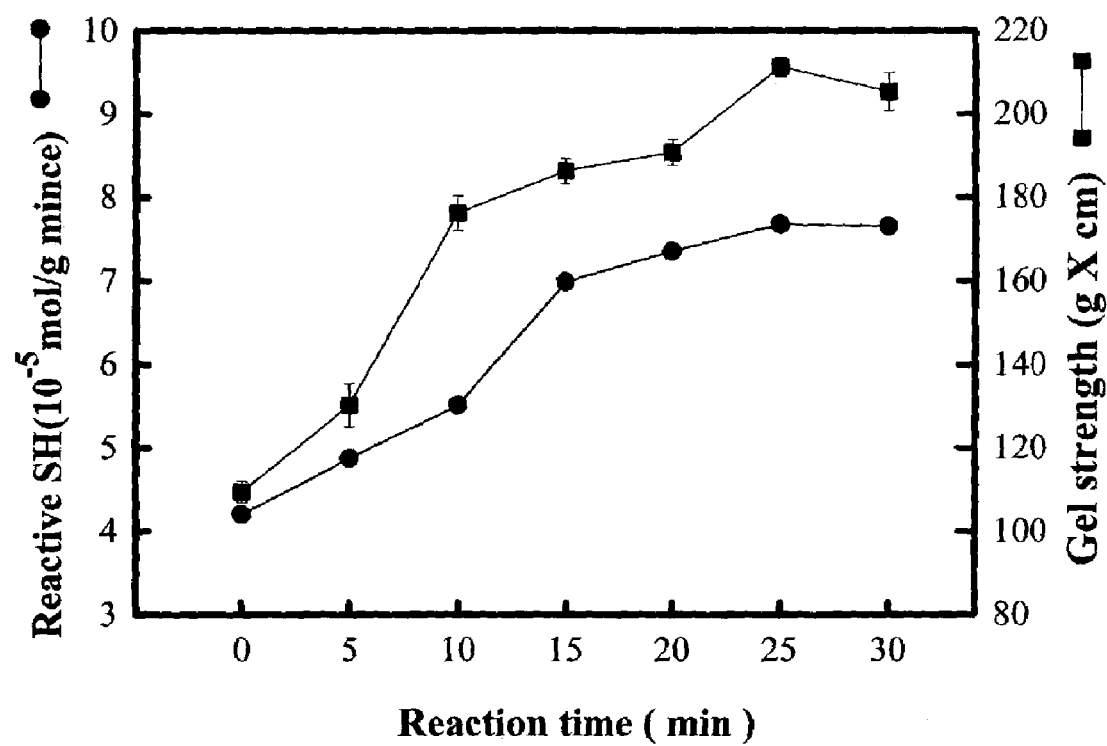
FIG. 5 shows the effects of the time for which the sulfite reductase from *Escherichia coli* acted on the meat of frozen denatured macerel surimi, on the number of reactive sulfhydryl groups and gel strength of the frozen denatured mackerel surimi. In the figure, "●" represents the number of the reactive sulfhydryl groups, and "■" represents the number of the gel strength.

The effects of the acting time of the sulfite reductase from *Escherichia coli* on frozen denatured mackerel surimi were indicated on FIG. 5. 0.03 active units/g mince of the sulfite reductase from *Escherichia coli* was added. The longer the acting time was, the more the number of reactive sulfhydryl groups increased obviously. The number of the reactive sulfhydryl groups increased from $4.20 \times 10^{-5}$ mol/g of control to $7.65 \times 10^{-5}$ mol/g mince after 25 minutes of incubation. Similar trends were also observed in the changes of the gel strength. The gel strength increased from 109.4 g×cm to 211.2 g×cm, and then tended to change gently.

Use Example 2

Figure 6:
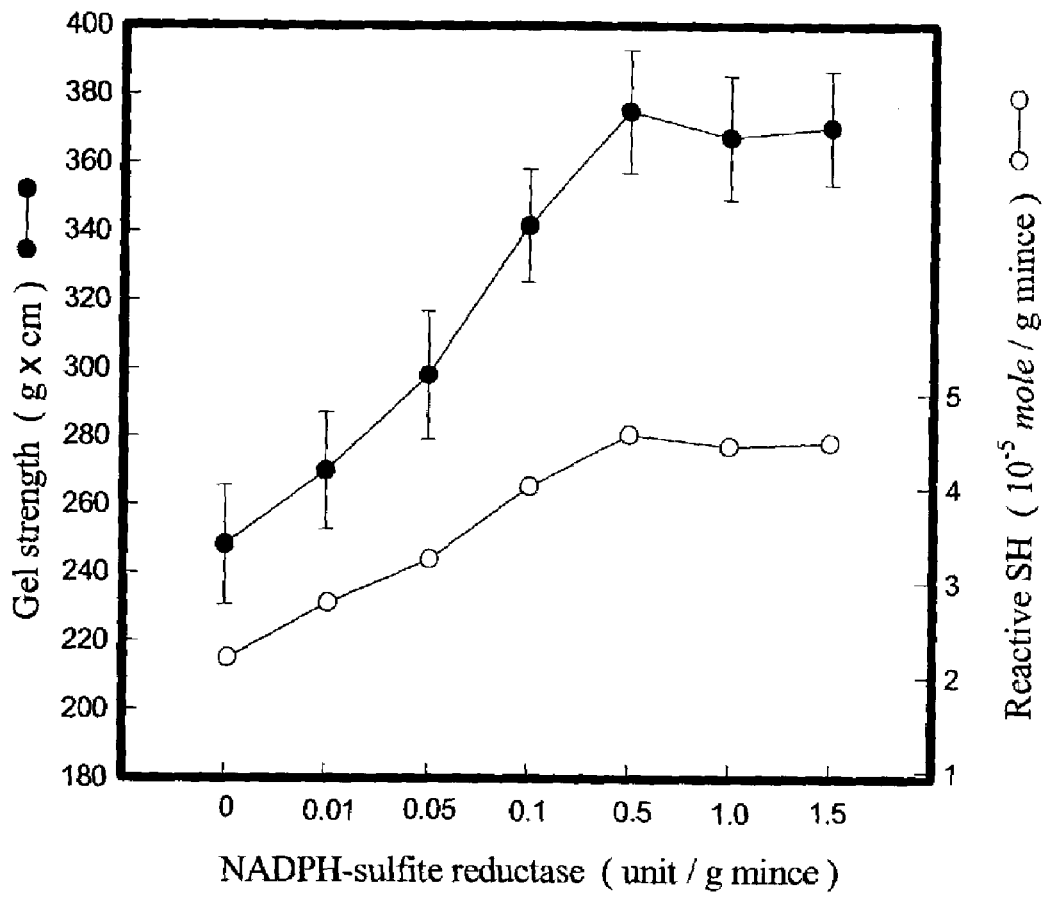
FIG. 6 represents the effects of the amount of the sulfite reductase from *Saccharomyces cerevisiae* added on the number of the reactive sulfhydryl groups and gel strength of ozonic decolored mackerel surimi. In the figure, "○" represents the number of the reactive sulfhydryl groups, and "●" indicates the gel strength.

Effects of the Sulfite Reductase from *Saccharomyces cerevisiae* on Frozen Denatured Mackerel Surimi Various active units of the sulfite reductase from *Saccharomyces cerevisiae* were added into frozen denatured mackerel surimi. The number of the reactive sulfhydryl groups in mackerel surimi increased obviously with the increase of the amount of the reductase added. When 0.5 units/g mince of the sulfite reductase from *Saccharomyces cerevisiae* was added, the number of the reactive sulfhydryl groups increased from $2.19 \times 10^{-5}$ mol/g of control to $3.48 \times 10^{-5}$ mol/g mince. Similar trends were also observed in the changes of the gel strength. As indicated on FIG. 6, the gel strength increased from 115.0 g×cm to 369.9 g×cm, when 0.5 units/g mince of the sulfite reductase from *Saccharomyces cerevisiae* was added.

The examples described above are given by way of illustration only and are not intended to limit this invention, various variations and modification can be made without departing from the spirit and the scope of the invention.

We claim:

1. A purified sulfite reductase having the following characteristics:
   a. it functions to catalyze the reduction of sulfites to sulfides or to recover the sulfhydryl groups from disulfide groups,
   b. in the aforesaid catalysis of the reduction, reduced nicotinamide adenine dinucleotide phosphate (NADPH), methyl viologen (MVH) or other donors act as an electron donor,
   c. its molecular weight is from 100,000 to 400,000,
   d. the optimal temperature for its activity is from 20° C. to 30° C.,
   e. the optimal pH for its activity is from 6.5 to 8.0, and
   f. said purified sulfite reductase is obtained from *Escherichia coil*.

2. The sulfite reductase as claimed in claim 1, wherein the electron donor is NADPH.

3. A process for producing purified sulfite reductase of claim 1 by employing ammonium sulfate fractionation and chromatography to purify the sulfite reductase from a crude enzyme solution of *Escherichia coil*.

4. The process for producing purified sulfite reductase as claimed in claim 3, wherein the crude enzyme solution is produced by the following steps:

adding a phosphate buffer of pH 6.5 to 8.5 to the cells of *Escherichia coil*;

disrupting the cells for 0.1 to 2 hours at a room temperature of 2° C. to 10° C. using an ultrasonic sonicator;

collecting the supernatant liquid after centrifugation for 30 minutes at 5,000 x g;

suspending the residual debris cells in the same buffer followed by grinding the debris cells;

collecting the supernatant liquid after aforementioned centrifugation; and combining the supernatant liquids.

5. The process for producing purified sulfite reductase as claimed in claim 4, wherein the ammonium sulfate fractionation comprises the following steps:

gently adding ammonium sulfate to the crude enzyme solution produced using the method steps of claim 4, collecting the precipitate at 30 to 60% saturation after centrifugation at a rate of 3,000 to 15,000 x g for 0.1 to 2 hours, dialyzing the solution of the precipitate against a 0.1 to 0.2 M phosphate buffer (pH 6.5 to 8.5) to obtain a dialysate, all the steps being performed at 2° C. to 10° C.

6. The process for producing sulfite reductase as claimed in claim 3, wherein the chromatography is selected from the group consisting of DEAE Sephacel column chromatography and/or Sephacryl S-300 HR column chromatography.

7. A method for recovering the proteins of denatured fish, comprising applying to the proteins of the denatured fish the sulfite reductase of claim 1 in solution or powder form in an amount of 0.01 to 0.5 active units of sulfite reductase per gram of the proteins of the denatured fish.

8. The method for recovering the proteins of denatured fish as claimed in claim 7, wherein the time for the sulfite reductase in solution or powder form to act on the proteins of the denatured fish is 5 to 40 minutes.

* * * * *